United States Patent [19]

Kuen

[11] Patent Number: 5,304,162
[45] Date of Patent: Apr. 19, 1994

[54] GARMENT AND PLEATED, ADJUSTABLE STRAP MEMBER THEREFOR

[75] Inventor: David A. Kuen, Neenah, Wis.

[73] Assignee: Kimberly-Clark Corporation, Neenah, Wis.

[21] Appl. No.: 998,696

[22] Filed: Dec. 30, 1992

[51] Int. Cl.$^5$ ............................................. A61F 13/15
[52] U.S. Cl. ...................................... 604/391; 2/221; 2/312; 2/325; 604/385.1; 604/392; 604/394
[58] Field of Search ................. 604/385.1, 385.2, 387, 604/389–392, 394; 2/237, 221, 312, 315, 325, 338

[56] References Cited

U.S. PATENT DOCUMENTS

| | | | |
|---|---|---|---|
| 1,245,655 | 11/1917 | Allen . | |
| 1,494,044 | 5/1924 | Ward et al. . | |
| 2,516,951 | 4/1947 | Brink | 128/287 |
| 2,548,162 | 4/1951 | Karels | 128/284 |
| 2,564,094 | 5/1946 | Brandl | 128/284 |
| 2,566,139 | 4/1950 | Ostrovsky et al. | 128/284 |
| 2,827,052 | 3/1958 | Goodman et al. | 128/284 |
| 3,081,772 | 3/1963 | Brooks et al. | 128/287 |
| 3,110,312 | 11/1963 | Wirth | 128/287 |
| 3,141,461 | 7/1964 | Farris | 128/284 |
| 3,150,664 | 9/1964 | Noel | 128/287 |
| 3,196,511 | 7/1965 | Kintner | 24/204 |
| 3,359,980 | 12/1967 | Rosenblatt | 128/284 |
| 3,441,024 | 4/1969 | Ralph | 128/287 |
| 3,441,025 | 4/1969 | Ralph | 128/287 |
| 3,452,753 | 7/1969 | Sanford | 128/287 |
| 3,455,303 | 7/1969 | Wilson | 128/289 |
| 3,460,535 | 8/1969 | Behna | 128/288 |
| 3,530,859 | 9/1970 | Heimowitz | 128/284 |
| 3,618,608 | 11/1971 | Brink | 128/287 |
| 3,653,381 | 4/1972 | Warnken | 128/284 |
| 3,728,191 | 4/1973 | Wierzba et al. | 156/265 |
| 3,882,871 | 5/1975 | Taniguchi | 128/287 |
| 3,955,575 | 5/1976 | Okuda | 128/284 |
| 4,051,854 | 10/1977 | Aaron | 128/284 |
| 4,145,763 | 3/1979 | Abrams et al. | 2/403 |
| 4,158,363 | 6/1979 | Schaar | 604/390 |
| 4,171,239 | 10/1979 | Hirsch et al. | 156/461 |
| 4,241,462 | 12/1980 | Tagawa et al. | 2/406 |
| 4,259,957 | 4/1981 | Sonenstein et al. | 128/287 |
| 4,299,223 | 11/1981 | Cronkrite | 128/287 |
| 4,315,508 | 2/1982 | Bolick | 128/289 |
| 4,338,938 | 7/1982 | Seavitt | 128/284 |

(List continued on next page.)

FOREIGN PATENT DOCUMENTS

| | | |
|---|---|---|
| 0276970A2 | 8/1988 | European Pat. Off. . |
| 0278866A1 | 8/1988 | European Pat. Off. . |
| 0287388A2 | 10/1988 | European Pat. Off. . |
| 0319249A1 | 6/1989 | European Pat. Off. . |
| 0321232A1 | 6/1989 | European Pat. Off. . |
| 0321234A1 | 6/1989 | European Pat. Off. . |
| 0330793A1 | 9/1989 | European Pat. Off. . |
| 0345014A3 | 12/1989 | European Pat. Off. . |
| 0374730A2 | 6/1990 | European Pat. Off. . |
| 2335165 | 8/1977 | France . |
| 2586558A1 | 3/1987 | France . |
| 63-2708 | 1/1988 | Japan . |
| 493819 | 10/1938 | United Kingdom . |
| 1428572 | 3/1976 | United Kingdom . |
| 1430747 | 4/1976 | United Kingdom . |
| 2074011A | 10/1981 | United Kingdom . |
| 2144637A | 3/1985 | United Kingdom . |
| 2200530A | 8/1988 | United Kingdom . |
| 2201893A | 9/1988 | United Kingdom . |
| 2233876A | 1/1991 | United Kingdom . |
| 2242612A | 10/1991 | United Kingdom . |
| 2248379A | 4/1992 | United Kingdom . |
| WO85/03205 | 8/1985 | World Int. Prop. O. . |
| WO88/06014 | 8/1988 | World Int. Prop. O. . |
| WO88/07335 | 10/1988 | World Int. Prop. O. . |
| WO91/03220 | 3/1991 | World Int. Prop. O. . |
| WO91/08725 | 6/1991 | World Int. Prop. O. . |
| WO92/10957 | 7/1992 | World Int. Prop. O. . |

Primary Examiner—Randall L. Green
Assistant Examiner—Rob Clarke
Attorney, Agent, or Firm—Thomas M. Gage

[57] ABSTRACT

A pleated, adjustable strap member is useful in securing a garment to a wearer. The strap member has first and second strap ends and can be attached to the garment adjacent the strap ends. The strap member also includes an elastic region and a pleated region, both located between the strap ends. The pleated region includes at least one Z-fold that is maintained with a releasable bond.

25 Claims, 3 Drawing Sheets

U.S. PATENT DOCUMENTS

| | | | |
|---|---|---|---|
| 4,340,563 | 7/1982 | Appel et al. | 264/518 |
| 4,388,075 | 6/1983 | Mesek et al. | 604/385 |
| 4,402,690 | 9/1983 | Redfern | 604/391 |
| 4,405,297 | 9/1983 | Appel et al. | 425/72 S |
| 4,410,327 | 10/1983 | Baggaley | 604/391 |
| 4,445,242 | 5/1984 | Bowen | 5/484 |
| 4,475,912 | 10/1984 | Coates | 604/385 |
| 4,516,975 | 5/1985 | Mitchell | 604/385 A |
| 4,568,342 | 2/1986 | Davis | 604/391 |
| 4,578,072 | 3/1986 | Lancaster | 604/385 A |
| 4,578,073 | 3/1986 | Dysart et al. | 604/397 |
| 4,589,878 | 5/1986 | Mitrani | 604/392 |
| 4,592,118 | 6/1986 | DeWoskin | 24/444 |
| 4,596,568 | 6/1986 | Flug | 604/369 |
| 4,597,760 | 7/1986 | Buell | 604/397 |
| 4,597,761 | 7/1986 | Buell | 604/397 |
| 4,610,680 | 9/1986 | LaFleur | 604/385 A |
| 4,610,682 | 9/1986 | Kopp | 604/385 R |
| 4,615,695 | 10/1986 | Cooper | 604/385 A |
| 4,617,022 | 10/1986 | Pigneul et al. | 604/391 |
| 4,623,339 | 11/1986 | Ciraldo et al. | 604/359 |
| 4,630,320 | 12/1986 | Van Gompel | 2/406 |
| 4,641,381 | 2/1987 | Heran et al. | 2/400 |
| 4,662,037 | 5/1987 | Provost et al. | 24/447 |
| 4,663,220 | 5/1987 | Wisneski et al. | 428/221 |
| 4,670,012 | 6/1987 | Johnson | 604/390 |
| 4,680,030 | 7/1987 | Coates et al. | 128/391 |
| 4,681,581 | 7/1987 | Coates | 604/391 |
| 4,704,117 | 11/1987 | Mitchell | 604/391 |
| 4,710,414 | 12/1987 | Northrup et al. | 428/43 |
| 4,728,326 | 3/1988 | Gilles | 604/391 |
| 4,745,926 | 5/1988 | Hlusko | 128/134 |
| 4,753,649 | 6/1988 | Pazdernik | 604/389 |
| 4,761,318 | 8/1988 | Ott et al. | 428/85 |
| 4,770,917 | 9/1988 | Tochacek et al. | 428/95 |
| 4,773,906 | 9/1988 | Krushel | 604/391 |
| 4,776,068 | 10/1988 | Smirlock et al. | 24/442 |
| 4,781,966 | 11/1988 | Taylor | 428/152 |
| 4,794,028 | 12/1988 | Fischer | 428/100 |
| 4,798,603 | 1/1989 | Meyer et al. | 604/378 |
| 4,801,298 | 1/1989 | Sorenson et al. | 604/384 |
| 4,834,742 | 5/1989 | Wilson et al. | 604/389 |
| 4,835,795 | 6/1989 | Lonon | 2/408 |
| 4,846,815 | 7/1989 | Scripps | 604/391 |
| 4,847,134 | 7/1989 | Fahrenkrug et al. | 428/138 |
| 4,854,136 | 8/1989 | Coslovi et al. | 66/191 |
| 4,869,724 | 9/1989 | Scripps | 604/389 |
| 4,870,725 | 10/1989 | Dubowik | 24/442 |
| 4,884,713 | 12/1989 | Handler | 220/23.4 |
| 4,886,512 | 12/1989 | Damico et al. | 609/385.2 |
| 4,887,338 | 12/1989 | Handler | 24/306 |
| 4,887,339 | 12/1989 | Bellanger | 24/575 |
| 4,891,868 | 1/1990 | Watanabe | 24/691 |
| 4,894,060 | 1/1990 | Nestegard | 604/391 |
| 4,908,025 | 3/1990 | Ketchum, Jr. | 604/327 |
| 4,909,802 | 3/1990 | Ahr et al. | 604/385.1 |
| 4,909,879 | 3/1990 | Ball | 156/164 |
| 4,932,950 | 6/1990 | Johnson | 604/391 |
| 4,936,840 | 6/1990 | Proxmire | 604/385.2 |
| 4,937,887 | 7/1990 | Schreiner | 2/402 |
| 4,938,754 | 7/1990 | Mesek | 604/385.2 |
| 4,963,140 | 10/1990 | Robertson et al. | 604/389 |
| 4,964,860 | 10/1990 | Gipson et al. | 604/391 |
| 4,973,326 | 11/1990 | Wood et al. | 604/391 |
| 4,981,480 | 1/1991 | Gaudet et al. | 604/386 |
| 4,988,346 | 1/1991 | Pfefferkorn | 604/389 |
| 4,994,054 | 2/1991 | Pigneul et al. | 604/391 |
| 5,019,073 | 5/1991 | Roessler et al. | 604/391 |
| 5,021,111 | 6/1991 | Swenson | 156/264 |
| 5,026,450 | 6/1991 | Cucuzza et al. | 156/244.11 |
| 5,032,122 | 7/1991 | Noel et al. | 604/391 |
| 5,100,399 | 3/1992 | Janson et al. | 604/386 |
| 5,125,246 | 6/1992 | Shytles | 66/193 |
| 5,135,522 | 8/1992 | Fahrenkrug et al. | 604/385.1 |
| 5,182,156 | 1/1993 | Pape et al. | 604/390 |

GARMENT AND PLEATED, ADJUSTABLE STRAP MEMBER THEREFOR

BACKGROUND OF THE INVENTION

The present invention relates generally to the field of garments with attachment systems. More particularly, the invention pertains to an improved attachment system for maintaining a garment in the crotch region of a wearer.

The present invention is intended for use with a wide variety of garments that are to be worn in the crotch region. Such garments may include disposable absorbent articles, underwear, bathing suits, athletic supporters, prosthetics, or other personal care or health care garments. With particular reference to disposable absorbent articles, these articles include such things as incontinence garments, disposable diapers, briefs, training pants, or the like. Disposable articles for the absorption and containment of urine and other body exudates are generally unitary, preshaped or prefolded, and are comprised of a fluid pervious bodyside liner, a fluid impervious backing sheet, and an absorbent material disposed between the bodyside liner and the backing sheet. They generally include some type of attachment system for securing the garment to the body of the wearer.

The types of attachment systems used on disposable absorbent articles has varied widely. In some systems, the front and back waist sections are directly attached to one another with a fastener. In other attachment systems, the front and back waist sections are connected via a strap or belt. For example, the garment suspension system described in U.S. Pat. No. 4,315,508 to Bolick includes two elastic straps that are provided with buttons or other fastening means. The garment described in U.S. Pat. No. 4,617,022 to Pigneul et al. includes a removable belt that may be attached to the garment with hook-and-loop type fasteners.

In order to effectively absorb and contain urine and other body exudates, disposable absorbent articles must properly fit the body of the wearer. Due to cost constraints, garment manufacturers have not produced absorbent articles in an infinite number of sizes. Instead, garment manufactures have designed absorbent articles that are adjustable. In existing disposable absorbent garments, adjustability has been accomplished by providing a range of locations over which the front and back waist sections can be oriented relative to one another. In U.S. Pat. No. 4,728,326 to Gilles, for instance, a diaper is disclosed which has straps that include hook members at the ends of the straps. The hook members attach to a loop member, which extends across the entire back waist section of the diaper. Similarly, U.S. Pat. No. 4,801,298 to Sorenson et al. utilizes a hook-and-loop fastener with a loop strip extending across the front of the diaper, and U.S. Pat. No. 4,315,508 to Bolick discloses elastic straps with buttons that may be secured within any one of a series of button holes. See also U.S. Pat. Nos. 2,516,951 to Brink; 2,564,094 to Brandl; 2,566,139 to Ostrovsky et al.

The foregoing types of adjustable garments possess a significant drawback: the location at which the straps are attached to the garment must be changed in order to adjust the garment for a particular wearer. The straps, for example, may need to be attached at locations remote from the corners or longitudinal ends of the garment. Unfortunately, however, attaching the straps at such locations may detract from the proper orientation or position of the garment on the wearer. This is particularly significant for disposable absorbent articles, because a poorly fitting garment or an improperly adjusted garment can result in leakage.

SUMMARY OF THE INVENTION

In response to the discussed drawbacks and problems encountered in the past, a new strap member for use in securing a garment to a wearer has been discovered. A strap member according to this invention includes a first strap end and an opposite second strap end. Adjacent each of the first and second strap ends, the strap member can be attached to the garment. The strap member also includes an elastic region located between the first and second strap ends and a pleated region located between the first and second strap ends. The pleated region includes a first Z-fold that is maintained with a releasable bond. This aspect of the invention provides a strap member that is adjustable and will properly orient a garment on the wearer. The adjustability is obtained without having to attach the strap member to the garment at locations remote from the corners and longitudinal ends of the garment.

In particular embodiments, the pleated region also includes a second Z-fold, and the first and second Z-folds have different gathered lengths. The strength of the releasable bond is selected such that the releasable bond withstands the stresses applied to the strap member during normal use. The strength is also weak enough to permit the wearer to easily fracture the bond when the strap member needs to be lengthened. The wearer can lengthen the strap member by grasping it on either side of a Z-fold and pulling to fracture the releasable bond.

In another aspect, the invention relates to a garment including a garment shell and a pair of strap members. The garment shell includes a first end, an opposite second end, and longitudinal sides extending between the first and second ends. The garment shell also includes a first waist section adjacent the first end, a second waist section adjacent the second end, and a crotch section between the first and second waist sections. The garment shell is formed of a bodyside liner, an absorbent core, and a backing sheet attached to the bodyside liner and sandwiching the absorbent core therebetween. At least one attachment pad formed of a loop material is located in the first and second waist sections. The strap members each include a first strap end and an opposite second strap end. An elastic region, which is formed of a material capable of stretching to at least about 125 percent of its unstretched length, is located between the first and second strap ends. A pleated region of each strap member abuts the elastic region and is located between the first and second strap ends. The pleated region includes first and second Z-folds that are each maintained by releasable bonds. The strap members also include first and second hook patches that are attached adjacent the first and second strap ends, respectively. The first and second hook patches are releasably engageable with the at least one attachment pad. This aspect results in a garment that is adjustable and can be properly oriented on the wearer. Notably, the location at which the strap members are attached to the garment shell does not have to be changed in order to customize the size of the garment for a particular wearer.

Numerous features and advantages of the present invention will appear from the following description. In the description, reference is made to the accompanying drawings which illustrate a preferred embodiment of the invention. Such embodiment does not represent the full scope of the invention. Reference should therefore be made to the claims herein for interpreting the full scope of the invention.

DETAILED DESCRIPTION OF THE PREFERRED EMBODIMENT

Figure 1:
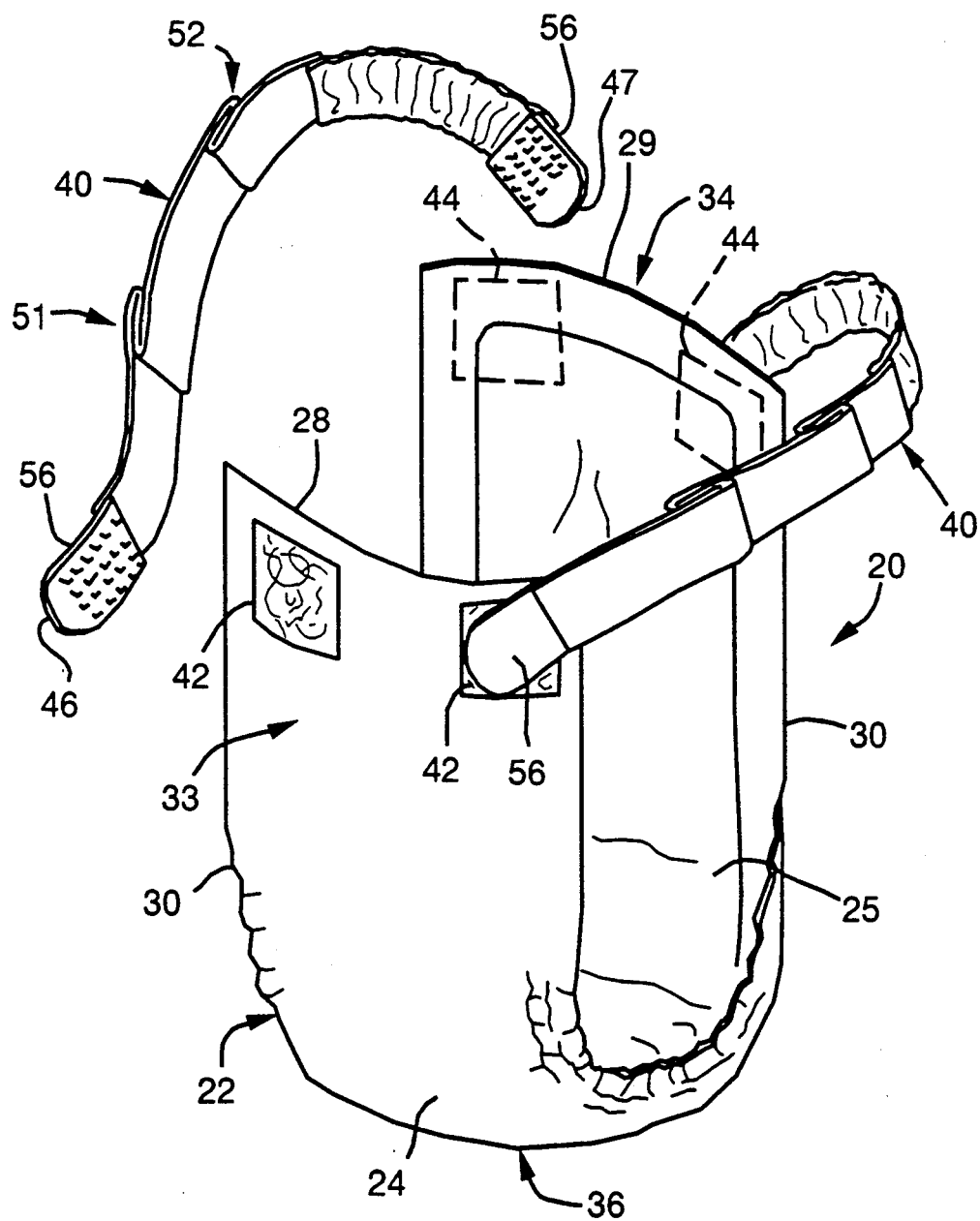
FIG. 1 is a partially-exploded perspective view of a disposable absorbent garment according to the present invention.
Figure 2:
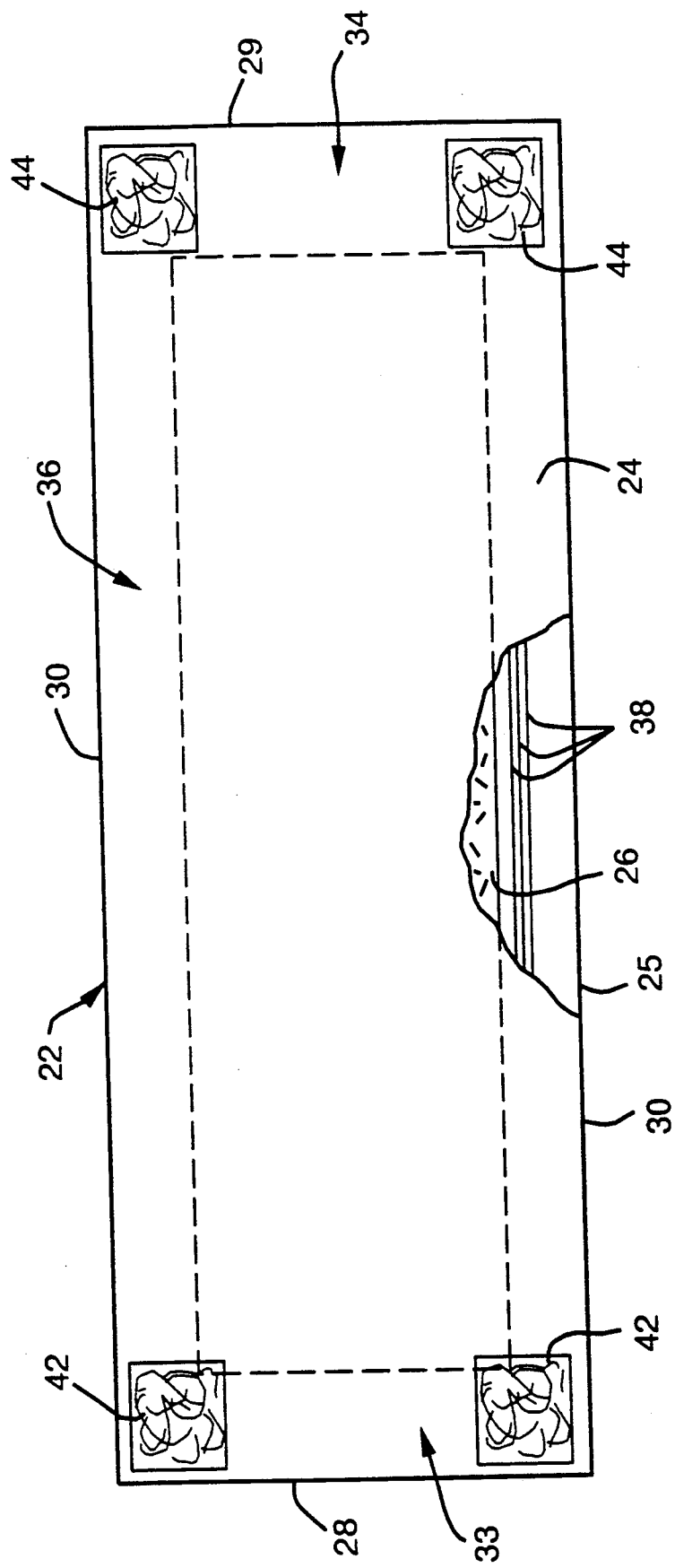
FIG. 2 is a plan view of a garment shell of the disposable absorbent garment shown in FIG. 1, with portions broken away for the purposes of illustration.

With reference to FIGS. 1 and 2, a disposable absorbent garment 20 formed according to the present invention is shown for purposes of illustration as an incontinence product for adults. The invention may also be embodied in other types of garments, such as other disposable absorbent articles, underwear, bathing suits, athletic supporters, prosthetics, or other personal care or health care garments.

The disposable absorbent garment 20 generally includes a garment shell 22 that is adapted to be used in conjunction with an attachment system. As shown, the shell 22 includes a substantially liquid impermeable backing sheet 24, a substantially liquid permeable bodyside liner 25, and an absorbent core 26 (FIG. 2) sandwiched between the backing sheet and the bodyside liner. The backing sheet 24 and bodyside liner 25 are preferably longer and wider than the absorbent core 26, so that the peripheries of the backing sheet and bodyside liner form margins which may be sealed together using ultrasonic bonds, adhesives, or other suitable means. The absorbent core 26 may be attached to the backing sheet 24 and/or the bodyside liner 25 using ultrasonic bonds, adhesives, or other suitable means. The garment 20 may also include additional components to assist in the acquisition, distribution and storage of waste material. For example, the garment 20 may include a transport layer, such as described in U.S. Pat. No. 4,798,603 to Meyer et al., which is incorporated herein by reference to the extent that it is consistent herewith.

The garment shell 22 as shown is generally rectangular with a first or front end 28, an opposite second or back end 29, and longitudinal sides 30 extending between the front and back ends. Corners of the garment shell 22 are formed a the intersections of the ends 28 and 29 and the longitudinal sides 30. The garment shell 22 also includes a first or front waist section 33 adjacent the front end 28 and an opposite second or back waist section 34 adjacent the back end 29. A crotch section 36 is located intermediate the front and back waist sections 33 and 34. When the garment shell 22 is placed on a wearer, the front waist section 33 is generally the portion of the garment located forward of the crotch region of the wearer, and the back waist section is generally the portion of the garment located rearward of the crotch region of the wearer. The garment shell 22 may be rectangular with a length in the range of from about 10 to about 34 inches (ca. 25-86 cm.), and a width in the range of from about 2 to about 22 inches (ca. 5-56 cm.). Of course, the garment shell 22 may optionally be T-shaped, I-shaped, hourglass-shaped, or irregularly-shaped.

The shell 22 may include elastic strands or ribbons 38 (FIG. 2) longitudinally orientated along each side margin of the garment 20 and attached in a stretched condition to the backing sheet 24, the liner 25, or both. The elastic strands 38 are located in the crotch section 36 and extend toward or into the front and back waist sections 33 and 34. The elastic strands 38 may assist in holding the shell 22 against the body of the wearer or forming seals or gaskets about the leg of the wearer.

The attachment system in the illustrated embodiment of the invention includes a pair of strap members 40, a pair of first or front attachment pads 42, and a pair of second or back attachment pads 44. The front and back attachment pads 42 and 44, which comprise the loop component of a hook-and-loop fastening system, may be identical in shape and formed of the same loop material. The term loop material is intended to mean a fabric having a base portion and a plurality of loop members extending upwardly from at least one surface of the base portion. The loop material can comprise a material manufactured to have a raised loop construction, stabilized through napping and thermosetting so that the individual loops are erect from the fabric base. The loop material may be formed of any suitable material, such as acrylic, nylon or polyester, and may be formed by methods such as warp knitting, stitch bonding or needle punching. The attachment pads 42 and 44 can also be any suitable material having non-woven loops thereon.

In a preferred embodiment, the attachment pads 42 and 44 have a two bar warp knit construction, with from 21 to 41 courses per inch (ca. 8-16 per cm.) and from 26 to 46 wales per inch (ca. 10-18 per cm.), of polyester yarn. In particular, about 15-35 percent of the yarns may be composed of yarn having about 1-30 individual filaments therein and having a yarn denier within the range of about 15-30 d (denier). In addition, about 65-85 percent of the yarns may be composed of yarn having about 1-30 individual filaments therein and having a yarn denier within the range of about 20-55 d. Also, the loops may particularly be formed with a loop height from about 2 to about 2.5 millimeters. The caliper may be from about 0.010 to about 0.040 inch (ca. 0.25-1 mm.) and the basis weight may be from about 1.0 to about 3.0 ounces per square yard (ca. 34-102 grams per square meter). One particular material which has been found suitable for the attachment pads 42 and 44 is identified as No. 19902 and is available from Guilford Mills of Greensboro, NC.

The front attachment pads 42 are located in the front waist section 33 and attached to the surface of the backing sheet 24 that is remote from the bodyside liner 25. The pads 42 are separated from one another and preferably spaced from the front end 28 and the longitudinal sides 30 by at least about 0.25 inch (ca. 6.5 mm.). Correspondingly, the back attachment pads 44 are located in the back waist section 34 and attached to the surface of the backing sheet 24 that is remote from the bodyside liner 5. The back attachment pads 44 are spaced from one another, and desirably although not necessarily spaced from both the second end 29 and the longitudinal sides 30 of the shell 22 by at least about 0.25 inch (ca. 6.5 mm.).

The geometric shape of the attachment pads 42 and 44 may take any form, such as square, rectangular, irregular, oval, round, etc. The size of the attachment pads 42 and 44 should be sufficient to be readily detectible by sight and touch. Desirably, each attachment pad is at least 1 inch by 1 inch (ca. 25 by 25 mm.), providing a surface area of at least about 6.25 square centimeters. It has been found, for example, that rectangular pads of approximately 1.25 inches by 3.38 inches (ca. 3 by 9 cm.) are desirable in the front waist section 28 and rectangular pads of approximately 1.5 inches by 2 inches (ca. 4 by 5 cm.) are desirable in the back waist section 29.

The attachment pads 42 and 44 are attached by ultrasonic bonds, adhesives, or other suitable means, so that the loops of the loop material extend outwardly from the backing sheet 24. The attachment pads may be aligned with the longitudinal or transverse axes of the garment 20. Alternately, the attachment pads may be attached at angles with respect to the longitudinal axis of the garment using a plurality of lines of adhesive (not shown), as disclosed in commonly assigned U.S. patent application Ser. No. 07/998,496, filed on the same date as the instant application, by D. A. Kuen et al. for a "Garment Attachment System".

As an alternative to using four attachment pads 42 and 44, two in the front waist section 33 and two in the back waist section 34, the attachment system could be constructed with a single attachment pad (not shown) that covers at least portions of both the front and back waist sections. Such a single attachment pad, formed of a loop material, could be attached to or formed integrally with the backing sheet 24. Still optionally, the attachment system could be constructed with a pair of attachment pads (not shown), one extending transversely across the front waist section 33 and one extending transversely across the back waist section 34.

Figure 3:
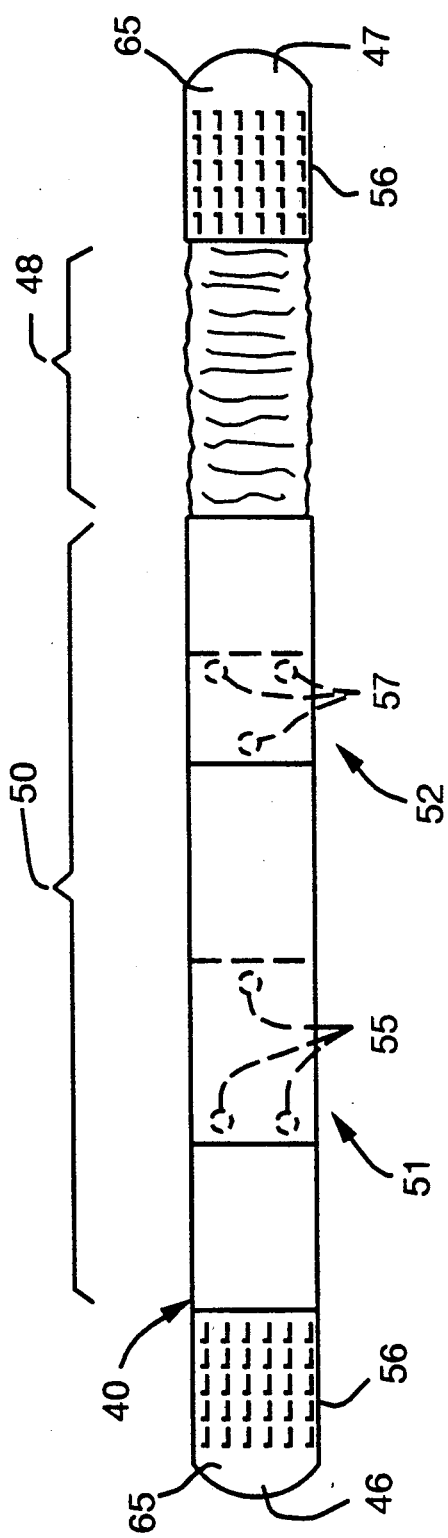
FIG. 3 is an enlarged plan view of a strap member of the disposable absorbent garment shown in FIG. 1.
Figure 4:
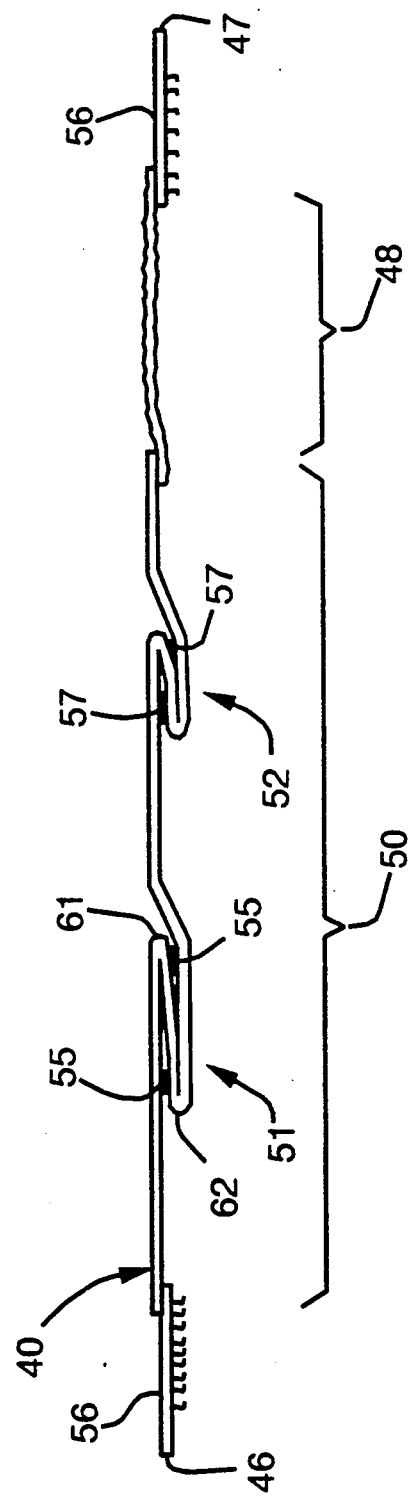
FIG. 4 is a top plan view of the strap member shown in FIG. 3, with portions shown in exaggerated size for purposes of illustration.

With additional reference to FIGS. 3 and 4, each strap member 40 has a first strap end 46 and an opposite second strap end 47. The length or longitudinal dimension of the strap extends between the strap ends 46 and 47. An elastic region 48 of each strap member 40 is located between the first and second strap ends 46 and 47. The elastic region 48 is formed of a material capable of stretching to at least about 1.25 times its unstretched length, desirably at least about 2.5 times its unstretched length, and thereafter substantially returning to its unstretched length. A pleated region 50 of each strap member 40 abuts the elastic region 48 and is located between the first and second strap ends 46 and 47. The pleated region 50 includes a first Z-fold 51 and a second Z-fold 52. The first and second Z-folds 51 and 52 are maintained by releasable bonds, illustrated in FIGS. 3 and 4 by reference numerals 55 and 57, respectively. Each strap member 40 also includes a hook patch 56 attached at or adjacent each strap end 46 and 47.

The pleated region 50 is desirably formed of a material that is soft, vapor-permeable and essentially nonelastic. This pleated material may be rectangular in shape, with a width of from about 0.5 to about 3 inches (ca. 1.27–7.62 cm.) and an overall length of from about 4 to about 18 inches (ca. 10.16–45.72 cm.), although other shapes are also possible. The length of the pleated material and the size of the Z-folds 51 and 52 will depend on the type of application for the strap member 40 and the size range of the wearer.

The pleated material has an overall length and an effective length. The overall length is the length of the material before it is folded. Conversely, the effective length is the length of the resulting pleated region 50 after the pleated material has been folded. Each of the first and second Z-folds 51 and 52 has a gathered length. As will be apparent, the sum of the gathered lengths of the Z-folds 51 and 52 represents the difference between the overall length and the effective length of the pleated material.

Each of the first and second Z-folds 51 and 52 is formed by folding the pleated material along two fold lines and securing the folds with the releasable bonds, designated 55 and 57 respectively. The fold lines are spaced apart from one another and are perpendicular to the longitudinal axis of the strap member 40. To illustrate, the first Z-fold 51 is formed by folding the pleated material along fold lines that are perpendicular to the longitudinal axis of the strap member 40 and located generally at regions designated 61 and 62 in FIG. 4. The gathered length of a Z-fold is equal to approximately twice the distance between the fold lines, so that the gathered length of the first Z-fold 51 is equal to twice the distance between points 61 and 62. The effective length of the pleated region 50, therefore, is the overall length of the pleated material less the gathered length of the first Z-fold 51 and less the gathered length of the second Z-fold 52.

By way of illustration, the overall length of the pleated material may be 15 inches (ca. 38.1 cm.), and the pleated material may include two Z-folds. The first Z-fold 51 is folded along fold lines that are separated by 2 inches (ca. 5.08 cm.) so that the first Z-fold has a gathered length of about 4 inches (ca. 10.16 cm.), and the second Z-fold 52 is folded along fold lines that are separate by 1.25 inches (ca. 3.18 cm.) so that the second Z-fold has a gathered length of about 2.5 inches (ca. 6.35 cm.). The effective length of the pleated region 50 is thus about 8.5 inches (ca. 21.59 cm.).

As illustrated in FIGS. 3 and 4, the releasable bonds 55 and 57 attach the pleated material to itself to create the effective length of the strap member 40. Accordingly, the releasable bonds 55 and 57 should be located near at least one of the fold lines. Preferably although not necessarily, the releasable bonds 55 and 57 are located near both of the fold lines, so that the folds assume a Z-shape in cross-sectional view (see FIG. 4). Each Z-fold 51 and 52 is illustrated as being releasably maintained by point or dot bonds 55 an 57. It should be appreciated that other patterns of releasable bonds, such as lines, areas, swirls and the like, may also be employed.

The strength of the releasable bonds 55 and 57 should be selected so that the bonds withstand the stresses applied to the strap members 40 during normal use of the garment 20. The strength of the bonds 55 and 57 should also be sufficiently weak to enable the wearer of the garment to fracture the bond if the strap members need to be lengthened for better garment fit. The strength of the bonds 55 and 57 may be measured by securing a portion of a strap member on one side of a Z-fold 51 or 52 to a fixed surface; attaching a weight to a portion of the strap member on the other side of the Z-fold 51 or 52; and gently positioning the weight such that it hangs from the fixed surface. For use of the strap member 40 on an adult absorbent garment 20 of the type illustrated, the releasable bonds 55 and 57 should remain intact, that is not fracture or fail, due to the force resulting from application of a weight of less than about 3 pounds (ca. 1,361 grams), but should break open, that is should fracture or fail, under the force resulting from application of a weight of more than about 24 pounds (ca. 10,886 grams). More desirably, the releasable bonds 55 and 57 should remain intact at forces less than about 14 pounds (ca. 6,350 grams), and should break open at forces more than about 18 pounds (ca. 8,165 grams).

In use, the releasable bonds 55 and 57 may be fractured or broken by grasping the strap member 40 on opposite sides of a Z-fold 51 or 52 and pulling apart, or otherwise releasing or breaking the bonds, such as by cutting. The wearer may also position himself or herself such that sufficient force is applied to the bonds to break open the bonds. The releasable bonds 55 and 57 may be adhesive bonds, cohesive bonds, ultrasonic bonds, thermal bonds, mechanical bonds such as snaps, rivets, staples, sewn stitches and hooks and loops, or other suitable bonds which meet the foregoing requirements. If desired, the releasable bonds of one Z-fold may be selected to break open under less force than would those of another Z-fold. In this way, only one Z-fold would break open at a time, even though a force was applied over the full length of the strap member 40.

The pleated material of the pleated region 50 is attached at one end to a hook patch 56 and at the other end to the elastic material of the elastic region 48. Similarly, the elastic material is attached at one end to the pleated material and at the other end to a hook patch 56. Attachment of the pleated and elastic materials, and attachment of the hook patches thereto, may be by ultrasonic bonds, adhesives, thermal bonds, stitches or other suitable means.

The hook patches 56 comprise a single-sided hook material and form the hook component of the hook-and-loop attachment system. The hook patches 56 may be of a variety of shapes, such as rectangular and measuring about 0.875 inch by about 1.125 inches (ca. 2.2 by 2.9 cm.). As illustrated in FIG. 3, each hook patch 56 may include a free end 65 that is rounded and void of hooks. The free end 65 provides a convenient surface for grasping the hook patch to remove it from engagement with loop material. As illustrated in FIGS. 1, 3 and 4, the hook patches 56 may be positioned such that the hook patches extent past the ends of the pleated material and the elastic material. In this case, the ends of the hook patches may be said to define the first and second strap ends 46 and 47. Alternately, the hook patches 56 may be positioned in full face-to-face contact with the strap members 40 (not shown), in which case the ends of the pleated and elastic materials may be said to define the first and second strap ends 46 and 47.

Suitable hook material may be molded or extruded of nylon, polypropylene or another suitable material. Desirable stiffness levels of the hook material may be obtained from polymeric materials having a flexural modulus of about 70,000–120,000 pounds per square inch (ca. $4.83 \times 10^8$–$8.27 \times 10^8$ nt/mz) and a Shore hardness value within the range of about D-40 to D-80, such as D-61. The hook patches 56 desirably contain uni-directional hooks, with the machine direction of the hooks aligned with the longitudinal axis of the strap member 40, and the hooks facing toward the opposite end portion 46 or 47 of the strap member. One suitable single-sided hook material for the hook patches is available from Velcro Industries B.V., Amsterdam, Netherlands or affiliates thereof, and is identified as HTH 708 with No. 22 uni-directional hook pattern.

The shape, density and polymer composition of the hooks may be selected to obtain desirable peel and shear force resistance values between the hook patches 56 and the attachment pads 42 and 44. One skilled in the art would recognize, for instance, that a more aggressive hook material may comprise a material with a greater average hook height, a greater percentage of directionally-aligned hooks, or a more aggressive hook shape. As one example, the density of the hook members may be more than 50 hooks per square inch (ca. 8 per square cm.), and more particularly within the range of about 440 to about 1040 hooks per square inch (ca. 68–161 per square cm.), such as about 740 hooks per square inch (ca. 115 per square cm.). The row density may be within the range of about 20 to about 60 rows per linear inch of width (ca. 8–24 per linear cm.), such as about 40 rows per linear inch of width (ca. 16 per linear cm.). The hook members may be hook-shaped, mushroom-shaped, arrow-shaped or any other desired shape.

In use, the garment shell 22 is positioned on the body of the wearer and secured in position using the attachment system. The first or front waist section 33 is located toward the front of the wearer, the second or back waist section 34 is located toward the posterior of the wearer, and the crotch section 36 is in place to receive body exudate. The wearer then engages one hook patch 56 on each strap member 40 with one of the back attachment pads 44. After stretching or relaxing the strap members 40 to obtain the desired tension therein, the wearer next engages the opposite hook patches 56 on each strap member 40 with one of the corresponding front attachment pads 42. The wearer can remove the strap members 40 by pulling on a portion of the strap near an attachment pad 42 or 44, or by pulling on a hook patch 56, such as at free end 65, to release the hook-and-loop engagement. Alternately of course, the strap members 40 could be secured to the garment shell 22 using other types of fasteners, such as buttons attached to the strap ends 46 and 47 and button holes formed in the front and back waist sections 33 and 34 (not shown).

The wearer can make modest adjustments to the tension in the strap members 40 by changing the location of the hook patches 56 on the attachment pads 42 and 44. If, however, the strap member 40 is entirely too small for the wearer, or the tension cannot be relieved by adjusting the location of the hook patches 56 on the attachment pads 42 and 44, the wearer can increase the effective length of the strap member by pulling apart one of the Z-folds 51 or 52. If the strap member 40 is then still too small, the wearer can again increase the effective length of the strap member by pulling apart the other Z-fold.

Desirably, the first and second Z-folds 51 and 52 have different gathered lengths. In this way, the wearer can select from three extended sizes of each strap member 40. For instance, if the first Z-fold 51 has a smaller gathered length than the second Z-fold 52, the wearer can pull apart only the first Z-fold 51 to increase the strap length by a first amount. Alternately, if a larger increase is anticipated, the wearer can pull apart only the second Z-fold 52 to increase the strap length by a larger amount. And finally, the wearer can pull apart both the first and second Z-folds 51 and 52 to increase the strap length a still larger amount.

As can be appreciated, the wearer can select from a wide variety of effective strap lengths to customize the fit of the garment 20. At any selected size, the strap members 40 continue to be extendable and hold the garment 20 firmly against the wearer, due to the elastic material of the elastic region 48. From an economic standpoint, the strap members 40 are particularly beneficial because of the relatively small amount of elastic material that is required. The strap members 40 are also beneficial from a production and packaging perspective in that a single strap design will accommodate a multitude of wearers.

A wide variety of materials may be used to construct the aforementioned components of the garment 20. The backing sheet 24, for example, may comprise a thin, substantially liquid impermeable web or sheet of plastic film such as polyethylene, polypropylene, polyvinyl chloride or similar material. The backing sheet material may be transparent or opaque and have an embossed or matte surface. One preferred material for the backing sheet 24 is a polyethylene film that has a nominal thickness of about 0.001 inch and a systematic matte embossed pattern, and that has been corona treated on both sides. Alternately, the backing sheet 24 may comprise a nonwoven, fibrous web which has been suitably constructed and arranged to be substantially liquid impermeable.

The bodyside liner 25 may be any soft, flexible, porous sheet which passes fluids therethrough. The bodyside liner 25 may comprise, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton. The bodyside liner 25 has a pore size that readily allows the passage therethrough of liquids, such as urine and other body exudates. The liner 25 may be selectively embossed or perforated with discrete slits or holes extending therethrough. Optionally, the web or sheet may be treated with a surfactant to aid in liquid transfer. One preferred bodyside liner material is a wettable spunbonded polypropylene having a basis weight of 0.7 ounces per square yard. Such material may be produced by the methods and apparatus described in U.S. Pat. Nos. 4,340,563 and 4,405,297 to Appel et al., which are incorporated herein by reference.

The absorbent core 26 is preferably an air-formed batt of cellulosic fibers (i.e., wood pulp fluff). One preferred type of wood pulp fluff, which is available under the trade designation CR2054 from Kimberly-Clark Corporation of Neenah, Wis., is a bleached, highly absorbent sulphate wood pulp containing softwood fibers. Optionally, the absorbent core 26 could comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers.

The absorbent core 26 may also include compounds to increase its absorbency, such as an effective amount of organic or inorganic high-absorbency materials. For example, the absorbent core 26 can include 0-95 weight percent high-absorbency material. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxpropyl cellulose, polyvinyl morpholinone, polymers and copolymers of vinyl sulfonic acid, polyacrylates, polyacylamides, polyvinyl pyridine and the like. Other suitable polymers can include hydrolyzed acrylonitrile grafted starch, acrylic acid grafted starch, and isobutylene maleic anhydride copolymers, and mixtures thereof. The hydrogel polymers are preferably sufficiently cross-linked to render the materials substantially water-insoluble. Cross-linking may, for example, be by irradiation or by covalent, ionic, van der Waals, or hydrogen bonding. Suitable materials are available from various commercial vendors, such as Dow Chemical Company, Celanese Corporation, and Allied-Colloid. Typically, the high-absorbency material is capable of absorbing at least about 15 times its weight in water, and preferably is capable of absorbing more than about 25 times its weight in water.

The high-absorbency material can be distributed or otherwise incorporated into the absorbent core 26 employing various techniques. For example, the high-absorbency material can be substantially uniformly distributed among the fibers comprising the absorbent core. The materials can also be nonuniformly distributed within the absorbent core fibers to form a generally continuous gradient with either an increasing or decreasing concentration of high-absorbency material, as determined by observing the concentration moving inward from the backing sheet 24. Alternatively, the high-absorbency material can comprise a discrete layer separate from the fibrous material of the absorbent core 26, or can comprise a discrete layer integral with the absorbent core.

Absorbent core 26 may also include a tissue wrap layer to help maintain the integrity of the fibrous core. This tissue wrap typically comprises a hydrophilic cellulosic material, such as creped wadding or a high wet-strength tissue.

The elastic strands 38 may be formed of a dry-spun coalesced multifilament elastomeric thread sold under the tradename LYCRA and available from I.E. Du Pont de Nemours and Company. Alternately, the leg elastic members 33 may be formed of other typical elastics utilized in the diaper-making art, such as a thin ribbon of natural rubber. Elasticity could also be imparted to the longitudinal side sections by extruding a hot melt elastomeric adhesive between the backing sheet 24 and the bodyside liner 25. Other suitable elastic gathering means are disclosed in U.S Pat. Nos. 4,938,754 to Mesek and 4,388,075 to Mesek et al.

The elastic material used to form the elastic region 48 may be composed of an elastomeric, cloth-like nonwoven fibrous material, such as an elastomeric stretch-bonded laminate web or an elastomeric meltblown web. In a particular aspect of the invention, the elastic material is composed of an elastomeric, nonwoven fibrous web that is soft and substantially vapor permeable.

Examples of suitable meltblown elastomeric fibrous webs for forming the elastic region 48 are described in U.S. Pat. No. 4,663,220 issued May 5, 1987, to T. Wisneski et al., which is incorporated herein by reference to the extent it is consistent herewith. Examples of composite fabrics comprising at least one layer of nonwoven textile fabric secured to a fibrous elastic layer are described in U.S. Pat. No. 4,781,966 issued Nov. 1, 1988, to J. Taylor et al., which is incorporated herein by reference to the extent that it is consistent herewith. The composite nonwoven fabrics are commonly referred to as stretch-bonded laminates.

In another aspect of the invention, the elastic material used to form the elastic region 48 can be composed of an elastomeric, stretchable composite web comprising individual, discrete strips of elastomeric materials secured to one or more nonwoven fibrous layers. Such a composite web may, for example, comprise an elastomeric meltblown material arranged in a selected pattern of strips and suitably sandwiched and attached between two layers of nonwoven, spunbond, fibrous material. The composite web may alternately comprise a selected pattern of individual elastomer strips operably secured to a nonwoven fibrous layer or between two nonwoven layers. The elastomer strips may, for example, be composed of a thermoplastic, melt extrudable material. Examples of suitable elastomer materials include polyether-polyamide block copolymers, polyurethanes, synthetic linear A-B-A and A-B block copolymers, chlorinated rubber/EVA (ethylene-vinyl acetate) blends, EPDM (ethylene-propylene diene monomer) rubbers, EPM (ethylene-propylene monomer) rubbers, blends of EPDM/EPM/EVA and the like. Still alternately, the elastic material may be composed of elastomeric threads or thin ribbons of natural rubber stretch-bonded between gatherable nonwoven layers, or composed of an interwoven polyester/rubber fabric with a nylon fluff backing sold by Shelby Elastics, Incorporated, of Shelby, N.C.

The pleated material used to form the pleated region 50 may be any soft, flexible sheet which can be folded and bonded to itself. Desirably, the pleated material is substantially vapor-permeable and essentially nonelastic. The pleated material may comprise, for example, a spunbond, meltblown or bonded-carded web composed of synthetic polymer filaments, such as polypropylene, polyethylene, polyesters or the like, or a web of natural polymer filaments such as rayon or cotton. One suitable material for the pleated region 50 is a spunbond polypropylene having a basis weight of about 2 ounces per square yard (ca. 68 grams per square meter.). Such material may be produced by the methods and apparatus described in U.S. Pat. Nos. 4,340,563 and 4,405,297 to Appel et al., which are incorporated herein by reference. Although presently less desirable from a cost standpoint, another option is to form the pleated region 50 of a pleated material that is itself an elastic material. In this case, the elastic and pleated regions 48 and 50 would simply represent different areas or zones of one or more elastic materials: the pleated region would comprise the portions where the elastic material is folded and bonded to itself, and the elastic region would comprise the portions where the elastic material is not folded.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, alternative fasteners, such as buttons with button holes, snaps, hooks, tapes and the like, may be substituted for the hook-and-loop fasteners illustrated herein. Further, the pleated region 50 may include three, four or more Z-folds. Likewise, the attachment system may be associated with garments other than the disposable absorbent garments as described herein. Therefore, the invention should not be limited by the specific embodiments described, but only by the claims.

I claim:

1. A strap member for use in securing a garment to a wearer, the strap member comprising:
    a first strap end;
    an opposite second strap end;
    means for attaching the strap member adjacent its first strap end to the garment;
    means for attaching the strap member adjacent its second strap end to the garment;
    an elastic region located between the first and second strap ends; and
    a pleated region located between the first and second strap ends, the pleated region comprising a first Z-fold that is maintained with a releasable bond which remains intact at forces less than about 3 pounds.

2. The strap member of claim 1 wherein the means for attaching the strap member adjacent its first and second strap ends comprises fasteners.

3. The strap member of claim 1 wherein the means for attaching the strap member adjacent its first and second strap ends comprises hook-and-loop fasteners.

4. The strap member of claim 1 wherein the pleated region further comprises a second Z-fold that is maintained with a releasable bond.

5. The strap member of claim 4 wherein the first and second Z-folds have different gathered lengths 6. The strap member of claim 1 wherein the releasable bond breaks open at forces greater than about 24 pounds.

7. A garment comprising:
    a garment shell having a first waist section, an opposite second waist section, and a crotch section between the first and second waist sections;
    a pair of strap members, each strap member comprising:
        a first strap end;
        an opposite second strap end;
        means for attaching the strap member adjacent its first strap end to the first waist section of the garment shell;
        means for attaching the strap member adjacent its second strap end to the second waist section of the garment shell;
        an elastic region located between the first and second strap ends; and
        a pleated region located between the first and second strap ends, the pleated region comprising a first Z-fold that is maintained with a releasable bond which remains intact at forces less than about 3 pounds.

8. The garment of claim 7 wherein the means for attaching each strap member adjacent its first and second strap ends comprises fasteners.

9. The garment of claim 7 wherein the means for attaching each strap member adjacent its first and second strap ends comprises hook-and-loop fasteners.

10. The garment of claim 7 wherein the pleated region of each strap member further comprises a second Z-fold that is maintained with a releasable bond.

11. The garment of claim 10 wherein the first and second Z-folds have different gathered lengths.

12. The garment of claim 7 wherein the releasable bond breaks open at forces greater than about 24 pounds.

13. The garment of claim 7 wherein the releasable bond remains intact at forces less than about 14 pounds and breaks open at forces greater than about 18 pounds.

14. A garment comprising:

a garment shell having a first end, an opposite second end, longitudinal sides extending between the first and second ends, a first waist section adjacent the first end, a second waist section adjacent the second end, and a crotch section between the first and second waist sections, the garment shell comprising:

a bodyside liner;

an absorbent core;

a backing sheet attached to the bodyside liner and sandwiching the absorbent core therebetween; and at least one attachment pad comprising a loop material and being located in the first and second waist sections; and a pair of strap members, each strap member comprising:

a first strap end;

an opposite second strap end;

an elastic region located between the first and second strap ends, the elastic region comprising a material capable of stretching to at least about 1.25 times its unstretched length;

a pleated region abutting the elastic region and located between the first and second strap ends, the pleated region comprising first and second Z-folds that are each maintained by a releasable bond at least one of said releasable bonds remains intact at forces less about 3 pounds;

a first hook patch attached adjacent the first strap end, the first hook patch being releasably engageable with the at least one attachment pad; and a second hook patch attached adjacent the second strap end, the second hook patch being releasably engageable with the at least one attachment pad.

15. The garment of claim 14 wherein the first and second Z-folds have different gathered lengths.

16. The garment of claim 14 wherein the releasable bonds break open at forces greater than about 24 pounds.

17. The garment of claim 16 wherein the releasable bonds remain intact at forces less than about 14 pounds and break open at forces greater than about 18 pounds.

18. The garment of claim 14 wherein the elastic region comprises a stretch bonded laminate.

19. The garment of claim 14 wherein the pleated region comprises an essentially nonelastic spunbond material.

20. A strap member for use in securing a garment to a wearer, the strap member comprising:

a first strap end;

an opposite second strap end;

means for attaching the strap member adjacent its first strap end to the garment;

means for attaching the strap member adjacent its second strap end to the garment;

an elastic region located between the first and second strap ends; and a pleated region located between the first and second strap ends, the pleated region being formed of an essentially nonelastic material and comprising a first Z-fold that is maintained with a releasable bond, the releasable bond remaining intact at forces less than about 3 pounds and breaking open at forces greater than about 24 pounds.

21. The strap member of claim 20 wherein the pleated region further comprises a second Z-fold that is maintained with a releasable bond, the first and second Z-folds have different gathered lengths.

22. A garment comprising:

a garment shell having a first waist section, an opposite second waist section, and a crotch section between the first and second waist sections; and a pair of strap members, each strap member comprising:

a first strap end;

an opposite second strap end;

means for attaching the strap member adjacent its first strap end to the first waist section of the garment shell;

means for attaching the strap member adjacent its second strap end to the second waist section of the garment shell.

an elastic region located between the first and second strap ends; and a pleated region located between the first and second strap ends, the pleated region being formed of an essentially nonelastic material and comprising a first Z-fold that is maintained with a releasable bond, the releasable bond remaining intact at forces less than about 3 pounds and breaking open at forces greater than about 24 pounds.

23. The garment of claim 22 wherein the pleated region of each strap member further comprises a second Z-fold that is maintained with a releasable bond, the first and second Z-folds have different gathered lengths.

24. The garment of claim 22 wherein the releasable bond remains intact at forces less than about 14 pounds and breaks open at forces greater than about 18 pounds.

25. The garment of claim 22 wherein:

the garment shell comprises at least one attachment pad formed of a loop material and located in the first and second waist sections;

the elastic region of each strap member comprises a material capable of stretching to at least about 1.25 times its unstretched length;

the pleated region of each strap member abuts the elastic region and comprises first and second Z-folds that are each maintained by a releasable bond;

a first hook patch is attached adjacent each first strap end, the first hook patch being releasably engageable with the at least one attachment pad; and a second hook patch is attached adjacent each second strap end, the second hook patch being releasably engageable with the at least one attachment pad.

* * * * *